(12) United States Patent
Conover et al.

(10) Patent No.: US 7,462,458 B2
(45) Date of Patent: Dec. 9, 2008

(54) METHODS OF DETECTING OVARIAN NEOPLASIA

(75) Inventors: Cheryl A. Conover, Rochester, MN (US); Kimberly R. Kalli, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 315 days.

(21) Appl. No.: 10/514,571

(22) PCT Filed: May 15, 2003

(86) PCT No.: PCT/US03/15572

§ 371 (c)(1),
(2), (4) Date: Jul. 27, 2005

(87) PCT Pub. No.: WO2004/045364

PCT Pub. Date: Jun. 3, 2004

(65) Prior Publication Data

US 2005/0272034 A1   Dec. 8, 2005

Related U.S. Application Data

(60) Provisional application No. 60/380,622, filed on May 15, 2002.

(51) Int. Cl.
   *G01N 33/53* (2006.01)
(52) U.S. Cl. ...................................................... 435/7.1
(58) Field of Classification Search ................... 435/7.1
   See application file for complete search history.

(56) References Cited

U.S. PATENT DOCUMENTS

| | | |
|---|---|---|
| 4,034,074 A | 7/1977 | Miles |
| 4,098,876 A | 7/1978 | Piasio et al. |
| 4,233,402 A | 11/1980 | Maggio et al. |
| 5,296,347 A | 3/1994 | LaMotte, III |

OTHER PUBLICATIONS

GenBank Accession No. P13727 dated Jan. 1, 1990, 8 pages.
Auersperg et al., "The Biology of Ovarian Cancer," *Semin. Oncol.*, 1998, 25(3):281-304.
Ausubel et al. (eds.), "Immunology," *Short Protocols in Molecular Biology*, 1992, Chapter 11, Green Publishing Associates and John Wiley & Sons, pp. 11-1, through 11-54.
Balagopal et al., "Age effect on transcript levels and synthesis rate of muscle MHC and response to resistance exercise," *Am J. Physiol. Endocrinol. Metab.*, 2001, 280:E203-E208.
Chaurand et al., "Peptide and Protein Identification by Matrix-Assisted Laser Desorption Ionization (MALDI) and MALDI-Post-Source Decay Time-of-Flight Mass Spectrometry," *J. Am. Soc. Mass Spectrom.*, 1999, 10(2):91-103.
Chen and Xu, "Determination of lysophosphatidic acids by capillary electrophoresis with indirect ultraviolet detection," *J. Chromatogr. B.*, 2001, 753(2):355-363.
Chen et al., "Molecular Regulation of the IGF-Binding Protein-4 Protease System in Human Fibroblasts: Identification of a Novel Inducible Inhibitor," *Endocrinol.*, 2002, 143(4):1199-1205.
Christiansen et al., "The Proform of Eosinophil Major Basic Protein: A New Maternal Serum Marker for Down Syndrome," *Prenatal Diagnosis*, 1999, 19:905-910.
Christiansen et al., "Quantification and Characterization of Pregnancy-Associated Complexes of Angiotensinogen and the Proform of Eosinophil Major Basic Protein in Serum and Amniotic Fluid," *Clin. Chem.*, 2000, 46:1099-1105.
Cole et al., "The EBV-Hybridoma Technique and Its Application to Human Lung Cancer," *Monoclonal Antibodies and Cancer Therapy*, 1985, Alan R. Liss, Inc., pp. 77-96.
Cote et al., "Generation of human monoclonal antibodies reactive with cellular antigens," *Proc. Natl. Acad. Sci USA*, 1983, 80:2026-2030.
Conover et al., "Insulin-Like Growth Factor-Binding Protein-1 Expression in Cultured Human Bone Cells: Regulation by Insulin and Glucocorticoid," *Endocrinol.*, 1996, 137(8):3295-3301.
Conover et al., "Pregnancy-Associated Plasma Protein-A is the Insulin-Like Growth Factor Binding Protein-4 Protease Secreted by Human Ovarian Granulosa Cells and Is a Marker of Dominant Follicle Selection and the Corpus Luteum," *Endocrinol.*, 2001, 142(5):2155-2158.
Einhorn et al., "Prospective Evaluation of Serum CA 125 Levels for Early Detection of Ovarian Cancer," *Obstet. Gynecol.*, 1992, 80(1)14-18.
Folkman, "A New Link in Ovarian Cancer Angiogenesis: Lysophosphatidic Acid and Vascular Endothelial Growth Factor Expression," *J. Natl. Cancer Inst.*, 2001, 93(10):734-735.
Gevaert et al., "Protein identification based on matrix assisted laser desorption/ionization-post source decay-mass spectrometry," *Electrophoresis*, 22(9):1645-1651.
Giudice et al., "Identification and Regulation of the IGFBP-4 Protease and Its Physiological Inhibitor in Human Trophoblasts and Endometrial Stroma: Evidence for Paracrine Regulation of IGF-II Bioavailability in the Placental Bed during Human Implantation," *J. Clin. Endocrinol. Metab.*, 2002, 87(5):2359-2366.
Guatelli et al., "Isothermal, in vitro amplification of nucleic acids by a multienzyme reaction modeled after retroviral replication," *Proc. Natl. Acad. Sci. USA*, 1990, 87:1874-1878.
Gurian et al., "Major basic protein as a marker of malignant potential in trophoblastic neoplasia," *Am. J. Obstet. Gynecol.*, 1996, 175(3):632-637.
Holschneider et al., "Ovarian Cancer: Epidemiology, Biology, and Prognostic Factors," *Semin. Surg. Oncol.*, 2000, 19:3-10.
Huse et al., "Gerneration of a Large Combinatorial Library of the Immunoglobulin Repertoire in Phage Lambda," *Science*, 1989, 246:1275-1281.

(Continued)

*Primary Examiner*—Christopher H Yaen
(74) *Attorney, Agent, or Firm*—Fish & Richardson P.C.

(57) ABSTRACT

Methods for diagnosing ovarian neoplasia, monitoring ovarian cancer therapy, and monitoring progression of disease in subjects based on the level of the proform of major basic protein in biological samples from the subjects are described.

19 Claims, No Drawings

OTHER PUBLICATIONS

Jat and Sharp, "Cell Lines Established by a Temperature-Sensitive Simian Virus 40 Large-T-Antigen Gene Are Growth Restricted at the Nonpermissive Temperature," *Mol. Cell. Biol.*, 1989, 9(4):1672-1681.

Kalli et al., "Pregnancy-associated plasma protein-A (PAPP-A) expression and insulin-like growth factor binding protein-4 protease activity in normal and malignant ovarian surface epithelial cells," *Int. J.Cancer*, 2004, 110(5):633-640.

Köhler and Milstein, "Continuous cultures of fused cells secreting antibody of predefined specificity," *Nature*, 1975, 256:495-497.

Kozbor and Roder, "The production of monoclonal antibodies form human lymphocytes," *Immunology Today*, 1983, 4:72-79.

Kruk et al., "A Simplified Method to Culture Human Ovarian Surface Epithelium," *Lab. Invest.*, 1990, 63:132-136.

Lawrence et al., "The insulin-like growth factor (IFG)-dependent IGF binding protein-4 protease secreted by human fibroblasts in pregnancy-associated plasma protein-A," *Proc. Natl. Acad. Sci. USA*, 1999, 96:3149-3153.

Lewis, "PCR's Competitors Are Alive and Well and Moving Rapidly Towards Commercialization," *Genetic Engineering News*, 1992, 12(9):1-3.

Mukai et al., "Elevated serum levels of eosinophil major basic protein in patients with myeloproliferative disorders without eosinophilia," *Int. J. Hematol.*, 1997, 66(2):197-202.

Orsulic et al., "Induction of ovarian cancer by defined multiple genetic changes in a mouse model system," *Cancer Cell*, 2002, 1:53-62.

Oxvig et al., "Identification of Angiotensinogen and Complement C3dg as Novel Proteins Binding the Proform of Eosinophil Major Basic Protein in Human Pregnancy Serum and Plasma," *J. Biol. Chem.*, 1995, 270(23):13645-13651.

Oxvig et al., "Isolation and characterization of circulating complex between human pregnancy-associated plasma protein-A and proform of eosinophil major basic protein," *Biochim. Biophys. Acta*, 1994, 1201:415-423.

Oxvig et al., "Circulating Human Pregnancy-associated Plasma Protein-A is Disulfide-bridged to the Proform of Eosinophil Major Basic Protein," *J. Biol. Chem.*, 1993, 268(17):12243-12246.

Popken-Harris et al., "Expression, Purification, and Characterization of the Recombinant Proform of Eosinophil Granule Major Basic Protein," *J. Immunol.*, 1995, 155:1472-1480.

Popken-Harris et al., "Regulation and Processing of a Precursor Form of Eosinophil Granule Major Basic Protein (ProMBP) in Differentiating Eosinophils," *Blood*, 1998, 92(2):623-631.

Qin et al., "Double-monoclonal immunoflurometric assays for pregnancy-associated plasma protein A/proeosinophil major basic protein (PAPP-A/proMBP) complex in first-trimester maternal serum screening for Down syndrome," *Clin. Chem.*, 1997, 43:2323-2332.

Resnick-Silverman et al., "Retinoblastoma Protein and Simian Virus 40-Dependent Immortalization of Human Fibroblasts," *J. Virol.*, 1991 65(6):2845-2852.

"Screening for Ovarian Cancer"[online]. National Cancer Institute, 2003, [retrieved on May 8, 2003]. Retrieved from the Internet:<URL: www.cancer.gov/cancerinfo/pdq/screening/ovarian/healthprofessionals> pp. 1-7.

Wagner et al., Analysis of Pregnancy-Associated Major Basic Protein Levels Throughout Gestation, *Placenta*, 1993, 14:671-681.

Wasmoen et al., "Biochemical and Amino Acid Sequence Analysis of Human Eosinophil Granule Major Basic Protein," *J. Biol. Chem.*, 1988, 263(25):12559-12563.

Weiss, "Hot Prospect for New Gene Amplifier," *Science*, 254:1292-1293.

Welsh et al., "Analysis of gene expression profiles in normal and neoplastic ovarian tissue samples identifies candidate molecular markers of epithelial ovarian cancer," *Proc. Natl. Acad. Sci. USA*, 2001, 98(3):1176-1181.

Xiao et al., "Evaluation of Plasma Lysophospholipids for Diagnostic Significance Using Electrospray Ionization Mass Spectrometry (ESI-MS) Analyses," *Ann. N. Y. Acad. Sci.*, 2000, 905:242-259.

SEQUENCE LISTING

<160> NUMBER OF SEQ ID NOS: 1

<210> SEQ ID NO 1
<211> LENGTH: 222

-continued

```
<212> TYPE: PRT
<213> ORGANISM: Homo sapiens

<400> SEQUENCE: 1

Met Lys Leu Pro Leu Leu Leu Ala Leu Leu Phe Gly Ala Val Ser Ala
 1               5                  10                  15

Leu His Leu Arg Ser Glu Thr Ser Thr Phe Glu Thr Pro Leu Gly Ala
             20                  25                  30

Lys Thr Leu Pro Glu Asp Glu Glu Thr Pro Glu Gln Glu Met Glu Glu
         35                  40                  45

Thr Pro Cys Arg Glu Leu Glu Glu Glu Glu Trp Gly Ser Gly Ser
     50                  55                  60

Glu Asp Ala Ser Lys Lys Asp Gly Ala Val Glu Ser Ile Ser Val Pro
 65                  70                  75                  80

Asp Met Val Asp Lys Asn Leu Thr Cys Pro Glu Glu Glu Asp Thr Val
                 85                  90                  95

Lys Val Val Gly Ile Pro Gly Cys Gln Thr Cys Arg Tyr Leu Leu Val
                100                 105                 110

Arg Ser Leu Gln Thr Phe Ser Gln Ala Trp Phe Thr Cys Arg Arg Cys
            115                 120                 125

Tyr Arg Gly Asn Leu Val Ser Ile His Asn Phe Asn Ile Asn Tyr Arg
            130                 135                 140

Ile Gln Cys Ser Val Ser Ala Leu Asn Gln Gly Gln Val Trp Ile Gly
145                 150                 155                 160

Gly Arg Ile Thr Gly Ser Gly Arg Cys Arg Arg Phe Gln Trp Val Asp
                165                 170                 175

Gly Ser Arg Trp Asn Phe Ala Tyr Trp Ala Ala His Gln Pro Trp Ser
            180                 185                 190

Arg Gly Gly His Cys Val Ala Leu Cys Thr Arg Gly Gly Tyr Trp Arg
            195                 200                 205

Arg Ala His Cys Leu Arg Arg Leu Pro Phe Ile Cys Ser Tyr
            210                 215                 220
```

METHODS OF DETECTING OVARIAN NEOPLASIA

CROSS-REFERENCE TO RELATED APPLICATIONS

This application is a National Stage application under 35 U.S.C. §371 and claims benefit under 35 U.S.C. §119(a) of International Application No. PCT/US2003/015572 having an International Filing Date of May 15, 2003, which claims the benefit of U.S. Provisional Application Ser. No. 60/380,622 having a filing date of May 15, 2002.

TECHNICAL FIELD

This invention relates to methods for detecting ovarian neoplasia, and more particularly, using the proform of major basic protein (proMBP) to detect ovarian neoplasia.

BACKGROUND

Epithelial ovarian cancer, which accounts for ~90% of all ovarian cancer, is the most common cause of death from gynecologic malignancies and originates from the single layer of epithelial cells on the surface of the ovary (Holschneider et al., *Semin. Surg. Oncol.* 19:3-10, 2000; Orsulic et al., *Cancer Cell* 1:53-62, 2002). It has been proposed that repeated stimulation of these ovarian surface epithelial (OSE) cells in response to injury caused by ovulation may play an etiologic role in the development of epithelial ovarian cancer (reviewed in Auersperg et al., *Semin. Oncol.* 25:281-304, 1998).

Injury repair responses are controlled by a variety of growth factors, including the insulin-like growth factors (IGFs). The IGF system is a complex network of IGF peptides (IGF-I and IGF-II), transmembrane receptors that mediate the biological responses to IGFs, and high affinity binding proteins that modulate IGF actions. IGF binding protein (IGFBP) functions are multifaceted, and include limiting the bioavailability of IGFs, targeting IGFs to distinct tissues, local regulation of IGF action at the cellular level, and newly recognized IGF-independent effects. This regulatory system is further controlled by the activation of proteases specific for individual IGFBPs. For example, the IGF-sequestering and, therefore, inhibitory function of IGFBP-4 is abrogated by enzymatic cleavage in the central portion of the IGFBP-4 molecule, resulting in the release of IGF-I. An IGF-dependent IGFBP-4 protease produced by a variety of cell types, including human fibroblasts and ovarian granulose cells was recently identified as pregnancy-associated plasma protein-A (PAPP-A) (Lawrence et al., *Proc. Natl. Acad. Sci. USA* 96:3149-3153, 1999). This protein had no previously identified function, but is elevated in serum during pregnancy due to increased placental expression. It is now recognized that PAPP-A functions outside of pregnancy as well. Although its exact physiological role is unknown, PAPP-A appears to be involved in repair responses in the vasculature and the reproductive ovary.

SUMMARY

The invention is based on the identification of the precursor form of eosinophil major basic protein (proMBP) as a marker of ovarian neoplasia. As described herein, expression of proMBP is minimal in normal cells, while in malignant cells, expression of proMBP is increased and PAPP-A activity is decreased. Thus, proMBP levels can be assessed in biological samples to aid in the diagnosis of ovarian neoplasia, including benign and malignant tumors, and to monitor the treatment for ovarian cancer.

In one aspect, the invention features a method for detecting ovarian neoplasia in a subject. The method includes detecting the level of proMBP present in a biological sample from the subject; and comparing the level of proMBP in the sample to the level of proMBP present in a control population, wherein an increase in the level of proMBP in the subject relative to that of the control population is indicative of ovarian neoplasia in the subject. The method further can include detecting the level of CA 125 in the biological sample and comparing the level of CA 125 in the sample to the level of CA 125 present in the control population, wherein an increase in the level of proMBP and CA 125 in the subject relative to the control population is indicative of ovarian neoplasia. The method also can further include detecting the level of lysophosphatidic acid in the biological sample, and comparing the level of lysophosphatidic acid in the sample to the level of lysophosphatidic acid present in the control population, wherein an increase in the levels of proMBP and lysophosphatidic acid in the subject relative to the control population is indicative of ovarian neoplasia The biological sample can be selected from the group consisting of blood, plasma, serum, urine, follicular fluid, ascites, and saliva. Serum and ascites are particularly useful.

The level of proMBP can be detected immunologically (e.g., using a capture antibody and a detection antibody, wherein the detection antibody includes a label). The label can be a fluorophore (e.g., fluorescein, fluorescein isothiocyanate (FITC), phycoerythrin (PE), allophycocyanin (APC), or peridinin chlorophyll protein (PerCP)), biotin, an enzyme, or a radioisotope. The capture antibody can be attached to a solid substrate (e.g., a solid substrate selected from the group consisting of a bead and a microtiter plate). The capture antibody can be a polyclonal antibody. The detection antibody can be a monoclonal antibody.

In another aspect, the invention features a method of monitoring treatment for ovarian cancer in a subject. The method includes detecting the level of proMBP present in a biological sample from the subject; and comparing the level of proMBP in the sample to a baseline level of proMBP present in the subject before the treatment.

The invention also features a method for monitoring a subject for recurrence of ovarian cancer. The method includes detecting the level of proMBP present in a biological sample from the subject; and comparing the level of proMBP in the sample to a baseline level of proMBP present in the subject.

In yet another aspect, the invention features a method for detecting ovarian neoplasia in a subject. The method includes detecting the level of PAPP-A activity present in a biological sample from the subject; and comparing the level of PAPP-A activity in the sample to the level of PAPP-A activity present in a control population, wherein a decrease in the level of PAPP-A activity in the subject relative to that of the control population is indicative of ovarian neoplasia in the subject.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

In general, the invention provides methods of using proMBP as a marker for ovarian neoplasia. As used herein, "neoplasia" refers to abnormal new growth, which can be benign or malignant. ProMBP is a preprotein of 222 amino acids that includes a signal peptide of 16 or 17 residues, an acidic propiece (to residue 105), and the mature form of MBP (residues 106 to 222). MBP is the major cytotoxic protein in eosinophil granules. In the serum of pregnant women, proMBP circulates in a complex with PAPP-A and inhibits the protease activity of PAPP-A (cleavage of IGFBP-4). See GenBank® Accession No. P 13727 for the amino acid sequence of proMBP, which is set forth as follows: MKL-PLLLALLFGAVSALHLR-SETSTFETPLGAKTL-PEDEETPEQEMEETPCRELEEEEEWGSG-SEDASKKDGAVESISVPD MVDKNLTCPEEEDTVKVVGIPGCQTC-RYLLVRSLQTFSQAWFTCRRCYRGNLVSIHNFN INYRIQCSVSALNQGQVWIGGRITGSGR-CRRFQWVDGSRWNFAYWAAHQPWSRGGHC VAL-CTRGGYWRRAHCLRRLPFICSY (SEQ ID NO:1). As described herein, reduced IGFBP-4 proteolysis and induced expression of proMBP is correlated with the malignant status of ovarian cells. Consequently, levels of proMBP can be detected in biological samples and used to diagnose ovarian neoplasia, include benign and malignant tumors, monitor treatment for ovarian cancer, track progression of disease (e.g., remission of disease or reoccurrence of disease), or assess tumor burden in patients. The level of proMBP can be assessed by either measuring proMBP protein or message (mRNA) as described below. Alternatively, since proMBP is an inhibitor of PAPP-A, reduced proteolytic activity of PAPP-A can be used as a marker of ovarian neoplasia.

Methods of Using ProMBP as a Marker for Ovarian Neoplasia

In general, methods of the invention include measuring the level of proMBP in a biological sample from a patient (e.g., a human patient) and comparing the level of proMBP to that from a control population (e.g., the average level of proMBP from a plurality of non-pregnant subjects without ovarian neoplasia). Suitable biological samples for measuring proMBP levels include, for example, blood (including whole blood, plasma, and serum), urine, follicular fluid, ascites, and saliva Serum and ascites are particularly useful biological samples. In some embodiments, the biological sample is a tissue sample (e.g., a biopsy).

The presence of ovarian neoplasia can be diagnosed based on the level of proMBP relative to the control population. Thus, it is determined if proMBP levels are increased, decreased, or the same as that of the control population. An increase in proMBP levels relative to that of the control population is indicative of ovarian neoplasia. Additional factors that can be considered when diagnosing ovarian neoplasia (e.g., ovarian cancer) include, for example, family history of ovarian cancer or other genetic factors and the levels of other markers of ovarian cancer. For example, the level of CA125, a tumor-associated antigen, can be assessed in combination with the level of proMBP. Typically, a reference value of 30 or 35 U/mL of CA 125 designates a positive screening test. CA 125 levels can be measured using a radioimmunoassay (RIA). See, for example, Einhorn et al., *Obstet Gynecol* 80(1):14-8, 1992. Additional markers of ovarian cancer can include the level of serum lysophosphatidic acid (LPA) or expression levels of LPA receptors LPA(2) and LPA(3). LPA stimulates proliferation of ovarian cancer cells and is present in ascites of patients with ovarian cancer. LPA can be detected by capillary electrophoresis or mass spectrometry (e.g., electrospray ionization mass spectrometry). See, Chen and Xu, *J. Chromatogr. B. Biomed. Sci. Appl.* 753(2):355-63, 2001; and Xiao et al., *Ann. N.Y. Acad. Sci.* 905:242-59, 2000. In addition, the levels of proMBP can be detected in combination with other techniques such as transvaginal ultrasonography or pelvic examinations.

The levels of proMBP in a subject also can be used to monitor treatment (e.g., chemotherapy or radiation) for ovarian cancer. Typically, the subject's baseline level of proMBP before treatment is compared to the level of proMBP at various time points after treatment (e.g., one or more days, weeks, or months after treatment). A decrease in proMBP levels relative to the baseline level is indicative of a positive response to treatment. Therapy can be monitored based on a combination of the subject's proMBP level and the level of other markers for ovarian cancer as described above. Similarly, a subject in remission from ovarian cancer can be monitored for reoccurrence of ovarian cancer by comparing levels of proMBP in the subject to the subject's baseline level of proMBP.

Detecting ProMBP

ProMBP can be detected, for example, immunologically using one or more antibodies. As used herein, the terms "antibody" or "antibodies" include intact molecules as well as fragments thereof that are capable of binding to an epitopic determinant of proMBP. The term "epitope" refers to an antigenic determinant on an antigen to which the paratope of an antibody binds. Epitopic determinants usually consist of chemically active surface groupings of molecules such as amino acids or sugar side chains, and typically have specific three-dimensional structural characteristics, as well as specific charge characteristics. Epitopes generally have at least five contiguous amino acids (a continuous epitope), or alternatively can be a set of noncontiguous amino acids that define a particular structure (e.g., a conformational epitope). The terms "antibody" and "antibodies" include polyclonal antibodies, monoclonal antibodies, humanized or chimeric antibodies, single chain Fv antibody fragments, Fab fragments, and F(ab)$_2$ fragments. Polyclonal antibodies are heterogenous populations of antibody molecules that are contained in the sera of the immunized animals. Monoclonal antibodies are homogeneous populations of antibodies to a particular epitope of an antigen.

Antibody fragments that have specific binding affinity for proMBP can be generated by known techniques. For example, F(ab')2 fragments that can be produced by pepsin digestion of the antibody molecule; Fab fragments can be generated by reducing the disulfide bridges of F(ab')2 fragments. Alternatively, Fab expression libraries can be constructed. See, for example, Huse et al., *Science* 246:1275 (1989). Once produced, antibodies or fragments thereof are tested for recognition of proMBP by standard immunoassay methods including ELISA techniques, radioimmunoassays, and Western blotting. See, *Short Protocols in Molecular Biology*, Chapter 1, Green Publishing Associates and John Wiley & Sons, Edited by Ausubel, F. M et al., 1992.

In immunological assays, an antibody having specific binding affinity for proMBP or a secondary antibody that binds to such an antibody can be labeled, either directly or indirectly. Suitable labels include, without limitation, radionuclides (e.g., $^{125}I$, $^{131}I$, $^{35}S$, $^{3}H$, $^{32}P$, $^{33}P$, or $^{14}C$), fluorescent moieties (e.g., fluorescein, FITC, PerCP, rhodamine, or PE), luminescent moieties (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). Antibodies can be indirectly labeled by conjugation with biotin then detected with avidin or streptavidin labeled with a molecule described above. Methods of detecting or quantifying a label depend on the nature of the label and are known in the art. Examples of detectors include, without limitation, x-ray film, radioactivity counters, scintillation counters, spectrophotometers, colorimeters, fluorometers, luminometers, and densitometers. Combinations of these approaches (including "multi-layer" assays) familiar to those in the art can be used to enhance the sensitivity of assays.

Immunological assays for detecting proMBP can be performed in a variety of known formats, including sandwich assays, competition assays (competitive RIA), or bridge immunoassays. See, for example, U.S. Pat. Nos. 5,296,347; 4,233,402; 4,098,876; and 4,034,074. Methods of detecting proMBP generally include contacting a biological sample with an antibody that binds to proMBP and detecting binding of proMBP to the antibody. For example, an antibody having specific binding affinity for proMBP can be immobilized on a solid substrate by any of a variety of methods known in the art and then exposed to the biological sample. Binding of proMBP to the antibody on the solid substrate can be detected by exploiting the phenomenon of surface plasmon resonance, which results in a change in the intensity of surface plasmon resonance upon binding that can be detected qualitatively or quantitatively by an appropriate instrument, e.g., a Biacore apparatus (Biacore International AB, Rapsgatan, Sweden). Alternatively, the antibody is labeled and detected as described above. A standard curve using known quantities of proMBP can be generated to aid in the quantitation of proMBP levels.

In other embodiments, a "sandwich" assay in which a capture antibody is immobilized on a solid substrate is used to detect the level of proMBP. The solid substrate can be contacted with the biological sample such that any proMBP in the sample can bind to the immobilized antibody. The level of proMBP bound to the antibody can be determined using a "detection" antibody having specific binding affinity for proMBP and the methods described above. It is understood that in these sandwich assays, the capture antibody should not bind to the same epitope (or range of epitopes in the case of a polyclonal antibody) as the detection antibody. Thus, if a monoclonal antibody is used as a capture antibody, the detection antibody can be another monoclonal antibody that binds to an epitope that is either completely physically separated from or only partially overlaps with the epitope to which the capture monoclonal antibody binds, or a polyclonal antibody that binds to epitopes other than or in addition to that to which the capture monoclonal antibody binds. If a polyclonal antibody is used as a capture antibody, the detection antibody can be either a monoclonal antibody that binds to an epitope that is either completely physically separated from or partially overlaps with any of the epitopes to which the capture polyclonal antibody binds, or a polyclonal antibody that binds to epitopes other than or in addition to that to which the capture polyclonal antibody binds. Sandwich assays can be performed as sandwich ELISA assays, sandwich Western blotting assays, or sandwich immunomagnetic detection assays. In some embodiments, a polyclonal antibody having affinity for the mature form of MBP can be used to capture both the pro- and mature forms of MBP. In this instance, proMBP can be detected using an antibody (e.g., a monoclonal antibody) having specific binding affinity for the pro portion of MBP.

Suitable solid substrates to which an antibody (e.g., a capture antibody) can be bound include, without limitation, microtiter plates, tubes, membranes such as nylon or nitrocellulose membranes, and beads or particles (e.g., agarose, cellulose, glass, polystyrene, polyacrylamide, magnetic, or magnetizable beads or particles). Magnetic or magnetizable particles can be particularly useful when an automated immunoassay system is used.

Antibodies having specific binding affinity for proMBP are available. See, for example, Chen et al, *Endocrinology* 143: 1199, 2002; Giudice et al, *J Clin Endocrinol Metab* 87:2359, 2002; Conover et al, *Endocrinology* 142:2155, 2001; Christiansen et al, *Prenatal Diagnosis* 19:905, 1999; Oxvig et al, *J Biol Chem* 270:13645, 1995; Popken-Harris et al., *Blood* 92(2):623-31, 1998; and Wagner et al, *Placenta* 14:671, 1993.

Alternatively, antibodies having specific binding affinity for proMBP can be produced through standard methods. In general, a proMBP polypeptide can be recombinantly produced, or can be purified from a biological sample, and used to immunize animals. As used herein, the term "polypeptide" refers to a polypeptide of at least 5 amino acids in length. To produce a recombinant proMBP polypeptide, a nucleic acid sequence encoding a proMBP polypeptide can be ligated into an expression vector and used to transform a bacterial or eukaryotic host cell. Nucleic acid constructs typically include a regulatory sequence operably linked to a proMBP nucleic acid sequence. Regulatory sequences do not typically encode a gene product, but instead affect the expression of the nucleic acid sequence. In bacterial systems, a strain of *Escherichia coli* such as BL-21 can be used. Suitable *E. coli* vectors include the pGEX series of vectors that produce fusion proteins with glutathione S-transferase (GST). Transformed *E. coli* are typically grown exponentially, then stimulated with isopropylthiogalactopyranoside (IPTG) prior to harvesting. In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

Mammalian cell lines that stably express a proMBP polypeptide can be produced by using expression vectors with the appropriate control elements and a selectable marker. For example, the eukaryotic expression vector pCDNA.3.1+ (Invitrogen, San Diego, Calif.) is suitable for expression of a proMBP polypeptide in, for example, COS cells, Chinese hamster ovary (CHO), or HEK293 cells. Following introduction of the expression vector by electroporation, DEAE dextran, or other suitable method, stable cell lines are selected. Alternatively, proMBP can be transcribed and translated in vitro using wheat germ extract or rabbit reticulocyte lysase.

In eukaryotic host cells, a number of viral-based expression systems can be utilized to express a proMBP polypeptide. A nucleic acid encoding a proMBP polypeptide can be cloned into, for example, a baculoviral vector and then used to transfect insect cells. Alternatively, the nucleic acid encoding a proMBP polypeptide can be introduced into a SV40, retroviral or vaccinia based viral vector and used to infect host cells. ProMBP polypeptides can be purified, using chromatographic techniques. See, for example, Oxvig et al, *J Biol Chem* 270:13645, 1995.

Various host animals can be immunized by injection of the proMBP polypeptide. Host animals include rabbits, chickens, mice, guinea pigs and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Monoclonal antibodies can be prepared using a proMBP polypeptide and standard hybridoma technology. In particular, monoclonal antibodies can be obtained by any technique that provides for the production of antibody molecules by continuous cell lines in culture such as described by Kohler, G. et al., *Nature*, 256:495 (1975), the human B-cell hybridoma technique (Kosbor et al., *Immunology Today* 4:72 (1983); Cole et al., *Proc. Natl. Acad. Sci USA*, 80:2026 (1983)), and the EBV-hybridoma technique (Cole et al., "Monoclonal Antibodies and Cancer Therapy", Alan R. Liss, Inc., pp. 77-96 (1983)). Such antibodies can be of any immunoglobulin class including IgG, IgM, IgE, IgA, IgD, and any subclass thereof. The hybridoma producing the monoclonal antibodies of the invention can be cultivated in vitro and in vivo.

Alternative techniques for detecting proMBP include mass-spectrophotometric techniques such as electrospray ionization (ESI), and matrix-assisted laser desorption-ionization (MALDI). See, for example, Gevaert et al., *Electrophoresis* 22(9):1645-51, 2001; Chaurand et al., *J Am Soc Mass Spectrom* 10(2):91-103, 1999. Mass spectrometers useful for such applications are available from Applied Biosystems (Foster City, Calif.); Bruker Daltronics (Billerica, Mass.) and Amersham Pharmacia (Sunnyvale, Calif.).

Detecting proMBP Nucleic Acids proMBP message can be detected, for example, by a polymerase chain reaction (PCR) assay. In general, PCR refers to amplification of a target nucleic acid, using sequence information from the ends of the region of interest or beyond to design oligonucleotide primers that are identical or similar in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. PCR is described, for example in *PCR Primer: A Laboratory Manual*, Ed. by Dieffenbach, C. and Dveksler, G, Cold Spring Harbor Laboratory Press, 1995. Nucleic acids also can be amplified by ligase chain reaction, strand displacement amplification, self-sustained sequence replication or nucleic acid sequence-based amplification. See, for example, Lewis, R., *Genetic Engineering News*, 12(9):1 (1992); Guatelli et al., *Proc. Natl. Acad. Sci. USA*, 87:1874-1878 (1990); and Weiss, R., *Science*, 254:1292 (1991).

For example, the levels of proMBP mRNA can be detected using reverse transcription-polymerase chain reaction (RT-PCR). RT-PCR has been shown to be 1,000-10,000 fold more sensitive than traditional RNA blotting techniques, and can detect and quantitate proMBP mRNA in tissue samples. Real-time quantitative PCR can be performed using, for example, the ABI PRISM 7700 Sequence Detection System and Taqman fluorogenic probes, or the LightCycler™ instrument from Roche. An internal reference can be used, such as amplification of the 28S rRNA with limiting primer concentration. This method allows quantitation down to approximately 500 copies of the target sequence. See, for example, Chen et al., *Endocrinology*, 143:1199-1205, 2002).

Detection of PAPP-A Activity

In some embodiments, PAPP-A activity is detected as a marker for ovarian neoplasia. PAPP-A activity can be detected by examining IGFBP-4 proteolytic activity in a biological sample. For example, a detectably labeled substrate can be incubated in the presence of the biological sample under suitable conditions, and proteolytic products then can be detected. The substrate can be, for example, IGFBP-4 or a fragment thereof. In general, the reaction can be carried out at 37° C. in a buffer such as 2 mM $CaCl_2$/50 mM Tris (pH 7.5), including IGF-II or fragments thereof, or any other protease activator. IGFII binds to IGFBP-4 such that IGFBP-4 is more susceptible to cleavage by PAPP-A. Typically, the substrate is labeled radioactively with isotopes such as $^{125}I$ or $^{32}P$, or non-radioactively labeled with biotin, digoxygenin, or a fluorophore. Proteolysis of IGFBP-4 is detected, for example, by examining proteolysis products, such as the 18 and 14 kDa reaction products of IGFBP-4. Radioactive proteins can be separated by reducing 15% SDS/PAGE and visualized by autoradiography. Proteolytic cleavage products also can be detected by immunoblotting.

PAPP-A activity also can be detected after capturing PAPP-A with polyclonal or monoclonal antibodies immobilized, for example, in a well of a microtiter plate. After washing away unbound protein of the biological sample, the activity of PAPP-A can be measured with a low molecular weight synthetic substrate that liberates a colored product that can be detected spectrophotometrically. IGF-II or other activator of PAPP-A can be added with the substrate.

Additionally, PAPP-A activity can be detected by incubating the sample in a well that contains immobilized substrate, e.g., IGFBP-4. Substrate is specifically labeled, i.e., radioactively or non-radioactively. Upon proteolytic cleavage of the substrate, labeled fragments are liberated into the liquid phase and can be detected. Substrate can be immobilized, for example, by coating with antibodies or IGF-II.

Labeling can also be accomplished by using IGFBP-4 expressed with different tags on the N-terminus or C-terminus of the protein, for example an N-terminal FLAG tag and a C-terminal c-myc tag. This allows IGFBP-4 to be immobilized with a monoclonal antibody that binds one of these tags. Detection of bound IGFBP-4 can then be accomplished by standard ELISA methodology using, for example, a peroxidase conjugated monoclonal antibody that recognizes the other tag. IGFBP-4 can also be immobilized and detected using monoclonal antibodies that recognize the N-terminus and the C-terminus, respectively. Proteolytic activity will result in a decreased signal, dependent on the amount of proteinase activity and time of incubation.

Articles of Manufacture

Antibodies having specific binding affinity for proMBP can be combined with packaging material and sold as a kit for diagnosing ovarian neoplasia, monitoring ovarian cancer therapy, or monitoring progression of disease. Components and methods for producing articles of manufactures are well known. The articles of manufacture may combine one or more anti-proMBP antibodies or fragments thereof as described herein. In addition, the articles of manufacture may further include reagents for measuring levels of other ovarian cancer markers in a biological sample, including, for example, CA 125 (e.g., antibodies having specific binding affinity for CA 125 antigen) or LPA (e.g., reagents for measuring LPA by capillary electrophoresis or electrospray ionization mass spectrometry), secondary antibodies, buffers, indicator molecules, solid phases (e.g., beads) and/or other useful agents for diagnosing ovarian neoplasia, monitoring ovarian cancer therapy, or monitoring progression of disease. The anti-proMBP antibody can be in a container, such as a plastic, polyethylene, polypropylene, ethylene, or propylene vessel that is either a capped tube or a bottle. Reagents for measuring levels of CA 125 or LPA can be included in separate containers. Instructions describing how the various reagents are effective for diagnosing ovarian neoplasia, monitoring ovarian cancer therapy, or monitoring progression of disease also may be included in such kits.

The invention will be further described in the following examples, which do not limit the scope of the invention described in the claims.

EXAMPLES

Materials and Methods

Cell Cultures

Normal OSE cultures were obtained from women undergoing oophorectomy for reasons unrelated to gynecologic malignancy. The ovaries were rinsed in sterile saline and the surface scraped with the blunt edge of a scapel. The cells were lysed immediately for RNA preparation or placed into culture. OSE cultures were obtained according to the procedures established by Kruk et al. (*Lab. Invest.* 63:132-136, 1990) in a 1:1 mix of MCDB 105:Medium 199 (Sigma-Aldrich Corp., St. Louis, Mo.) supplemented with 15% fetal bovine serum (FBS; Irvine Scientific, Santa Ana, Calif.) and antibiotics (Life Technologies, Grand Island, N.Y.). At first or second passage, cultures with cobblestone morphology were exposed for 24 h to the retrovirus pZipSVtsA58 encoding the temperature-sensitive mutant of the SV40 large T antigen in the presence of 8 µg/ml polybreen, generating OSE(tsT) lines. Cells were incubated at 34° C. upon exposure to the virus and were not drug selected. Unmodified OSE cultures senesce between passages 4 and 6, and undergo obvious and previously characterized morphological changes that accompany the decrease in growth rate (see Kruk et al., 1990, supra). OSE(tsT) cells, on the other hand, maintain the atypical morphology and continue to grow to passage 20-22.

Both OSE and OSE(tsT) cultures were characterized by immunohistochemistry with antibodies recognizing the epithelial marker cytokeratin, the intermediate filament vimentin that is expressed by epithelial cells of mesenchymal origin as well as by fibroblasts, and the endothelial marker factor VIII. All cultures used, whether unmodified or infected with pZipSVtsA58, were uniformly cytokeratin positive, vimentin positive, and factor VIII negative. The ages of the patients providing samples used to generate the five OSE cultures and four OSE(tsT) cultures used in these studies are provided in Table 1. Patient ages indicate age at time of oophorectomy or ovarian tumor debulking. Tumor morphology and grade were confirmed by a pathologist according to FIGO standards. Disease stage was obtained from a review of the pathology report from the surgery.

TABLE 1

Patient characteristics for tissue samples used to generate short-term normal and malignant ovarian surface epithelial cell cultures.

| Culture type: | Age | Ovarian pathology |
|---|---|---|
| OSE | | |
| OSE-33 | 34 | normal |
| OSE-40 | 39 | normal |
| OSE-41 | 37 | normal |
| OSE-42 | 47 | normal |
| OSE-45 | 48 | normal |
| OSE(tsT) | | |
| OSE(tsT)-14 | 48 | normal |
| OSE(tsT)-124 | 60 | normal |
| OSE(tsT)-125 | 47 | normal |
| OSE(tsT)-130 | 45 | normal |
| Tumor | | |
| OV1023 | 68 | grade 4 serous; stage IV |
| OV1025 | 49 | grade 2 endometrioid; recurrent disease |
| OV1029 | 60 | grade 3 serous, stage III |
| OV1037 | 86 | grade 3 serous, stage III |
| OV1072 | 79 | grade 3 serous, stage IV |
| OV1099 | 46 | grade 4 serous, stage III |

Short-term tumor cultures were initiated by manual disruption of ovarian tumors obtained from five women with previously undiagnosed ovarian cancer and one patient with recurrent disease (Table 1) during surgical debulking and disease staging in the Mayo Clinic Surgical Suites. Cells were plated in α-MEM Earles Salts nucleosides supplemented with 20% fetal bovine serum, 2 mM L-glutamine, and antibiotics. Fibroblast colonies were manually removed from the plates when feasible. Cultures were characterized by immunohistochemical staining as described for OSE cells. Only cultures that are >99% epithelial based on cytokeratin staining were used. Normal patient samples were coded for anonymous use and tumor samples used after obtaining informed consent as approved by the Mayo Clinic Institutional Review Board.

Cell-conditioned Media

Serum-free cell-conditioned media (CM) were obtained from monolayer cultures at 80-100% confluency. Serum-containing media were aspirated and monolayers washed 3 times with phosphate-buffered saline. Serum-free medium (SFM) consisting of phenol-red free DMEM supplemented with 0.1% bovine serum albumin, antibiotics and glutamine was added and incubation continued for 24-72 h. At harvest, CM was removed to a centrifuge tube and centrifuged at 2500 rpm for 15 minutes at 4° C. before freezing in small aliquots at −80° C. OSE(tsT) cells were cultured in complete media for 72 h at 39° C. to minimize the effects of the SV40 large T antigen before being washed and changed to SFM when CM from cells at 39° C. were required.

Immunohistochemisty

Cells were grown on chamber slides in complete medium until at least 80% confluency. Slides were fixed for 10 minutes in ice-cold acetone, air-dried, and stored at −80° C. prior to staining. After blocking endogenous peroxidase, slides were blocked with DAKO protein block. Anti-cytokeratin AE1/AE3 (Boehringer Mannheim, Indianapolis, Ind.) and anti-SV40 large T antigen (Biogenesis, Inc., Brentwood, N.J.) antibodies or isotype-matched mouse $IgG_1$ (Research Diagnostics, Inc. Flanders, N.J.) as a negative control were added for 30 minutes at room temperature followed by washes in water. Biotinylated rabbit anti-mouse IgG and HRP-streptavidin were added sequentially and slides washed before development with AEC substrate solution (Dako) and counterstaining.

Northern Analysis

OSE(tsT) cell lines were held at 34° C. (for SV40LT-positive OSE(tsT) cells) or 39° C. (for SV40LT-negative OSE (tsT) cells) for 48 h after which total RNA (20 µg) was prepared, size-fractionated through a 1.5% agarose gel containing 2.2 M formaldehyde, and transferred to nylon membranes (Nytran, Schleicher and Schuell, Keene, N.H.) as previously described (Conover et al., *Endocrinol.*, 137:3295-3301, 1996). RNA integrity was assessed by UV shadowing. The membranes were UV autocross-linked, prehybridized at 42° C. for 6 h, and hybridized at 42° C. overnight with $10^6$ cpm/ml $^{32}$P-labeled cDNA probe. Human IGFBP-4 cDNA (provided by Dr. S. Shimasaki, Whittier Institute, La Jolla, Calif.) was labeled with [$^{32}$P]deoxy-CTP using a random primed DNA labeling kit (New England Nuclear Corp., Boston, Mass.). Filters were washed twice for 15 min each in 6×SSPE (1×SSPE=0.15 M NaCl, 0.01 M $NaH_2PO_4$, and 1 mM EDTA, pH 7.4)-0.1% SDS at room temperature, twice for 15 min each in 1×SSPE-0.1% SDS at 65° C. Hybridization signals on the blots were analyzed quantitatively by densitometric scanning of autoradiograms after various exposure times.

IGFBP-4 Protease Assay

Fifty microliters of CM from OSE, OSE(tsT), or short-term tumor cultures were incubated with $^{125}$I-IGFBP-4 without or with 5 nM IGF-II (R&D Systems, Minneapolis, Minn.) at 37° C. Reaction products were fractionated by 7.5-15% linear acrylamide gradients using SDS-PAGE. Gels were dried and exposed to film or PhosphorImager (Molecular Dynamics, Sunnyvale, Calif.). In some experiments, CM were assayed in the presence of PAPP-A antiserum (aP) to inhibit PAPP-A or nonspecific rabbit IgG I.

RNA Isolation and cDNA Synthesis

The RNeasy Mini Kit (Qiagen Inc., Valencia, Calif.) was used to prepare total RNA from cell cultures. RNA was treated with DNase (DNA-free, Ambion, Austin, Tex.) before reverse transcription of 400 ng RNA using TaqMan Reverse Transcription Reagents (PE Applied Biosystems, Foster City, Calif.) according to the manufacturer's instructions. Absence of genomic DNA contamination was confirmed by PCR (see below) using isolated RNA without reverse transcription as template.

5' Nuclease Assay

The 5' nuclease assays (formerly referred to as Real-Time quantitative PCR analyses) were performed using the ABI PRISM 7700 Sequence Detection System, software, and all reagents from PE Applied Biosystems. Primer and probe sequences for specific amplification and detection of the targets (PAPP-A and proMBP) as well as the reference gene (nuclear DNA-encoded gene 28S rRNA, Balagopal et al., *Endocrinol. Metab.* 280:E203-E208, 2001) were as described by Chen et al., *Endocrinology*, 143:1199-1205, 2002). All samples were analyzed in triplicate and quantitated by normalizing the target signal with the 28S signal. PAPP-A and proMBP messages were detected from undiluted cDNA, while the optimal range of the 28S signal required ten- to fifty-fold dilution of the cDNA. Relative quantification of the target genes was performed by comparing the number of amplification cycles required by each gene to reach a fixed threshold of signal intensity ($C_T$), with more abundant mRNA yielding lower $C_T$. Relative abundance=$2^{\Delta CT}$, where $\Delta C_T$ is Reference $C_T$-Treatment $C_T$. Samples run without templates (as negative controls) went for 40 cycles without reaching threshold (i.e. $C_T$=40).

ELISAs

PAPP-A and proMBP were determined by sandwich biotin-tyramide amplified ELISAs, using a PAPP-A/proMBP polyclonal antibody for capture (Oxvig et al., *Biochim. Biophys. Acta* 1201:415-423, 1994; Christiansen et al., *Clin. Chem.*, 46:1099-1105, 2000) and a collection of PAPP-A monoclonal antibodies for detection of PAPP-A and a single proMBP monoclonal antibody for detection of proMBP (Qin et al., *Clin. Chem.* 43:2323-2332, 1997). The intra- and interassay coefficients of variation were 10% and 15% for the PAPP-A assay and 5% and 10% for the proMBP assay, respectively. The assays were calibrated against the WHO IRP 78/610 pregnancy serum standard for pregnancy proteins (Statens Serum Institut, Copenhagen, DK). The detection limits for the PAPP-A and proMBP assays were 0.03 mIU/L and 0.07 mIU/L, respectively.

Statistical Analysis

Statistical comparisons were performed using ANOVA and the Dunnett test for multiple comparisons to control. Results were considered statistically significant at P<0.05.

Example 1

Conditionally-Immortalized OSE(tsT) Cell Model

Normal human ovarian surface epithelial cells were infected with a retroviral construct encoding a temperature-sensitive mutant form of the SV40 large T antigen (Jat et al., *Mol. Cell. Biol.* 9:1672-1681, 1989), generating OSE(tsT) cultures. At the permissive temperature of 34° C. these cells proliferate and the cultures are expanded. At the restrictive temperature of 39° C., the mutated large T antigen is unstable and the cells cease to proliferate but remain viable. OSE(tsT) cells stain positively for cytokeratin (A1/A3) at both temperatures, indicating maintenance of their epithelial phenotype. The large T antigen is strongly apparent at the permissive temperature of 34° C., but decreases in staining intensity with increased time at the nonpermissive temperature (39° C.). Although staining is detectable for some time after the shift to 39° C., the heat-induced destabilization of the tsA58 mutant of the SV40 large T antigen results in abrogated ability to bind p53 (Resnick-Silverman et al., *J. Virol.* 65:2845-2852, 1991), thereby impairing interactions thought to be important for large T antigen effects on cell cycle.

The generation of OSE(tsT) cell lines, a lifespan-extended, pre-malignant OSE model system, addresses technical limitations inherent to the use of primary ovarian epithelia. This model system allowed reversible manipulation of the lines from "normal" to "transformed" conditions, elucidating a regulatory mechanism controlling PAPP-A and proMBP expression and IGFBP-4 proteolysis.

Example 2

IGFBP-4 Proteolysis in OSE(tsT) Cells

Steady-state levels of IGFBP-4 mRNA expression (as assessed by Northern blotting) and protein secretion were similar in OSE(tsT) cells grown at both 34° C. and 39° C., although absolute expression in OSE(tsT) lines obtained from two patients differed. However, IGF-dependent IGFBP-4 protease activity (defined as the loss of intact $^{125}$I-

IGFBP-4 substrate and generation of radiolabeled fragments of 18 and 14 kD only in the presence of IGF-II) in the medium of OSE(tsT) cells at 39° C. was greater than that at 34° C. IGF-dependent proteolysis of IGFBP-4 in medium conditioned by cells at 39° C. (SV40LT-negative cells) was apparent within 2 minutes of cell-free assay and complete by 20 min, whereas in medium from cells at 34° C. (SV40LT-positive cells) it was apparent at 20 min of assay and complete by 5 h. IGFBP-4 proteolysis in serum-free CM from four OSE (tsT) lines incubated at 39° C. was inhibited by polyclonal anti-PAPP-A antiserum, implicating PAPP-A as the IGF-dependent IGFBP-4 protease secreted by OSE(tsT).

Example 3

PAPP-A Expression and Activity in OSE(tsT) Cells

The 5' nuclease assay was used to quantitate PAPP-A mRNA in OSE(tsT) cells at each temperature, and showed that PAPP-A mRNA is expressed in OSE(tsT) cells cultured at 34° C. [$C_T$ 25.9±0.15; 10-fold diluted 28S $C_T$ 16.2±0.34]. Results (mean±SD of triplicate determinations) are expressed as abundance relative to the 24 h 34° C. sample. However, PAPP-A mRNA increased 2-fold, 3-fold, and 7-fold (1, 2, or 3 days after the temperature shift, respectively) after OSE (tsT) cells were changed to the restrictive temperature. The converse experiment (shift of cells at 39° C. to 34° C., allowing re-accumulation of the SV40 large T antigen) showed a 5-fold decrease in abundance in PAPP-A mRNA after 24 h and 48 h at 34° C., while cells at 39° C. maintained relatively constant levels of mRNA.

The accumulation of PAPP-A protein in the medium generally reflected the observed changes in mRNA levels. PAPP-A was detected at 3- to 5-fold higher levels in the conditioned media of OSE(tsT) cells moved to 39° C. for 1, 2, or 3 days than cells held at 34° C. (Table 2, Experiment 1, data are expressed as mIU/L/$10^5$ cells). In the converse experiment, cells held at 39° C. for 48 h accumulated more PAPP-A in the media than did cells moved to 34° C. (Table 2, Experiment 2, data are expressed as mIU/L/$10^5$ cells). Importantly, IGFBP-4 proteolysis, although verified to be blocked by antiserum recognizing PAPP-A, did not correlate with levels of PAPP-A protein determined by ELISA. For example, PAPP-A protein levels were equally high in 24-h CM from cells at 34° C. and 39° C. in Experiment 2 (Table 2), but the extent of IGF-II-dependent IGFBP-4 proteolysis differed. CM from OSE(tsT) cells at 39° C. had IGF-II-dependent proteolytic activity sufficient to decrease the intensity of the intact IGFBP-4 band by 62%, while that from cells at 34° C. cleaved 38% of the intact IGFBP-4 (data not shown). The decreased proteolytic activity at permissive temperature is despite a 26% increase in the number of cells held at 34° C. It was postulated that an additional factor, i.e., an inhibitor of IGFBP-4 proteolysis, also was being regulated.

These results indicate that normal, unmodified OSE cell cultures express abundant PAPP-A mRNA and protein. The observation that OSE cells produce PAPP-A is not limited to cultured cells, because uncultured human OSE cells express measurable levels of PAPP-A mRNA. Expression of this IGFBP-4 protease is consistent with the role of PAPP-A as a positive regulator of IGF-mediated signaling and growth. In this role, PAPP-A cleaves IGFBP-4 and reduces its affinity for IGFs, effectively increasing local IGF bioavailability. Without being bound to a particular mechanism, this could be a mechanism by which PAPP-A induces the proliferation of OSE cells after ovulation and subsequent repair of the ovulation-associated wound.

TABLE 2

PAPP-A levels in OSE conditioned media

| Experiment 1: PAPP-A ± temperature change from 34° C. → 39° C. | | |
|---|---|---|
| | Constant 34° C. | 34° C. → 39° C. |
| 24 h | 174 | 293 |
| 48 h | 282 | 658 |
| 72 h | 151 | 824 |
| Experiment 2: PAPP-A levels ± temperature change from 39° C. → 34° C. | | |
| | Constant 39° C. | 39° C. → 34° C. |
| 6 h | 586 | 522 |
| 24 h | 793 | 680 |
| 48 h | 1034 | 746 |

Example 4

ProMBP Expression and Action in OSE(tsT) Cells

To determine whether the discrepancy between PAPP-A proteolytic activity and protein detected by ELISA was explained by the induction of proMBP, expression of proMBP was analyzed in OSE(tsT) cells shifted from 39° C. to 34° C. OSE(tsT) cells after 72 h at the restrictive temperature (39° C.) expressed little proMBP mRNA relative to the 0 h control CT values ($C_T$ 32.3±0.13 for proMBP; ten-fold diluted 28S $C_T$ 20.2±0.07). However, cells changed to the permissive temperature showed a marked increase in proMBP mRNA that was apparent at 6 h and maximal (increased nearly 20-fold) at 24 h. ProMBP protein in the CM from cells held at 39° C. remained relatively constant (10 and 13 mIU/L/$10^5$ cells at 24 and 48 h, respectively), while protein in CM from cells moved to 34° C. increased to 26 and 44 mIU/L/$10^5$ cells at 24 h and 48 h, respectively, after the temperature change. The induction of proMBP coincided with decreased levels of IGF-dependent IGFBP-4 proteolysis in the 24-h CM from cells at 34° C.

Example 5

ProMBP Levels in Normal and Malignant Ovarian Epithelial Cells

The expression of SV40 large T antigen, while insufficient to immortalize OSE(tsT) cells, may still initiate processes involved in cellular transformation. Therefore, the levels of proMBP and PAPP-A expression and activity were analyzed in unmodified OSE cultures and short-term cultures of malignant epithelial cells obtained from ovarian tumors. PAPP-A and proMBP protein levels in CM were determined by ELISA as described in the Materials and Methods section. Primary cultures of normal OSE cells showed high levels of PAPP-A protein, undetectable proMBP protein in 4 of 5 OSE cultures (Table 3, data are expressed as mIU/L/$10^5$ cells), and abundant IGF-dependent IGFBP-4 protease activity in CM. These characteristics are similar to those of the conditionally-immortalized OSE(tsT) negative cells at 39° C. In comparison, while ovarian tumor cultures expressed variable levels of PAPP-A protein, they consistently had relatively high amounts of proMBP (Table 3) and little or no detectable IGFBP-4 protease activity in the medium. The pattern of malignant cells expressing higher levels of proMBP than normal OSE is maintained at the mRNA level in patient samples that were never exposed to artificial culture conditions. Thus, 3 of 3 pools of uncultured ovarian brushings had undetectable proMBP mRNA ($C_T$~40) while 5 of 5 frozen tumor samples expressed proMBP mRNA with $C_T$=34.9-36.4 (fifty-fold diluted 28S $C_T$ 18.9-19.3). Therefore, results from the cell culture system of both OSE and tumor cell cultures are reflected in patient samples from individuals without and with ovarian malignancies, and reveal an association between a malignant phenotype and higher levels of proMBP.

TABLE 3

PAPP-A and proMBP protein in short-term cultures of unmodified normal OSE and malignant ovarian epithelial cells

| | PAPP-A (mIU/L) | proMBP (mIU/L) |
|---|---|---|
| Normal OSE | | |
| OSE-33 | 761 | <1 |
| OSE-40 | 495 | <1 |
| OSE-41 | 367 | <1 |
| OSE-42 | 1302 | <1 |
| OSE-45 | 629 | 1.7 |
| Ovarian Tumor | | |
| OV-1023 | 1159 | 18.5 |
| OV-1025 | 1128 | 18.6 |
| OV-1029 | 408 | 2.2 |
| OV-1037 | 611 | 37.5 |
| OV-1072 | 23 | 2.9 |
| OV-1099 | 231 | 1.8 |
| Unconditioned serum-free media | <5 | <1 |

As indicated in Table 3, PAPP-A protein levels in CM from normal OSE cultures and short-term tumor cultures varies widely and does not demonstrate clear differences in PAPP-A protein expression that are dependent on whether the cells are normal or malignant. This may indicate that temporal changes in PAPP-A mRNA expression are more extreme than changes in protein expression, perhaps due to a relatively stable protein in vitro. Most importantly, PAPP-A protein levels did not correlate with the dramatically decreased proteolysis of IGFBP-4 consistently observed in CM from malignant cells.

Decreased proteolysis in CM from short-term tumor cultures and SV40LT-positive OSE(tsT) cells was associated with increased expression of proMBP. Unmodified OSE cultures and SV40LT-negative OSE(tsT) cells express little or no proMBP mRNA or protein, and have abundant proteolytic activity against IGFBP-4.

Example 6

Assay for Detecting proMBP

A two-site immunoradiometric assay (RIA) was developed for detection of proMBP. A panel of antibodies was screened using the FAST assay to find the antibody pair for optimal binding to proMBP, but not to MBP, good sensitivity and discrimination range, and minimal non-specific binding. Plates were coated with various antibodies (~1,000) then radiolabeled proMBP or radiolabeled MBP (as a negative control) was applied. After washing the plates, the amount of radiolabeled proteins was measured. By using this method, antibodies that bound proMBP strongly and MBP weakly were selected. After selecting a subset of antibodies, a RIA was performed using one antibody for coating and another antibody for detection of serial dilutions of proMBP and MBP. The antibody pair of 163-15E10 and 176-8H8 was chosen based on high sensitivity to proMBP and no or minimal cross-reactivity with MBP. See, Popken-Harris et al., *Blood* 92(2):623-31, 1998 for a description of the murine 163-15E10 monoclonal antibody.

Before RIA, standard proMBP and serum samples were reduced and alkylated to allow full detection of proMBP. Fifty microliters of samples were diluted with 130 µl Tris buffer (0.12M NaCl, 0.01M EDTA, 0.33M Tris aminomethane, pH8). Dithiothreitol (DTT), 20 µl of 0.1M solution in Tris buffer, was added and the mixture was incubated at room temperature for 60 minutes. Iodoacetamide, 20 µl of 0.02M solution in Tris buffer, was added and the incubation continued for an additional 20 minutes.

For RIA, Immulon-4 96-well plates (Dynatech Laboratories, Chantilly, Va.) were coated overnight at 4° C. with the capture antibody, 163-15E10 (100 µl at 10 µg/ml in PBS). The rest of incubation steps were performed at room temperature. Wells were washed with washing solution (0.1M $PO_4$, 0.1% Tween 20, pH 7.5). Unbound sites on the wells were then blocked with PPF-E buffer (0.1M $PO_4$, 0.5% fetal calf serum; 0.1% $NaN_3$, 0.01M EDTA, 1% protamine sulfate, pH 7.5). Buffers were removed and 100 µl of standard proMBP or unknown serum samples was placed in the wells. The proMBP standard curve ranged from 2 ng/ml to 1000 ng/ml. The standard and samples were incubated for 2 hours. After washing, 100 µl of $^{125}$I-labeled 176-8H8 antibody (50 ng/ml in PPF-E) was placed in the wells and incubated for 1 h. Wells were washed and counted in a gamma scintillation counter. The concentrations of proMBP in unknown samples were calculated by the spline curve fitting interpolation of standard proMBP.

Serum levels of proMBP were measured in women with ovarian tumors (n=10) and in normal controls (n=5). The ovarian cancer patients had mean proMBP levels of 203±19 ng/ml versus a mean value of 109±13 ng/ml for the normal controls. This difference in proMBP serum levels was determined to be statistically significant (p<0.01).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting ovarian neoplasia in a subject, said method comprising:
   a) detecting the level of proMBP present in a biological sample from said subject, wherein said proMBP comprises the amino acid sequence set forth in SEQ ID NO:1; and
   b) comparing the level of proMBP in said sample to the level of proMBP present in a control population, wherein an increase in the level of proMBP in said subject relative to that of said control population is indicative of ovarian neoplasia in said subject.

2. The method of claim 1, said method further comprising detecting the level of CA 125 in said biological sample and comparing the level of CA 125 in said sample to the level of CA 125 present in said control population, wherein an increase in the level of proMBP and CA 125 in said subject relative to said control population is indicative of ovarian neoplasia.

3. The method of claim 1, said method further comprising detecting the level of lysophosphatidic acid in said biological sample, and comparing the level of lysophosphatidic acid in said sample to the level of lysophosphatidic acid present in said control population, wherein an increase in the levels of proMBP and lysophosphatidic acid in said subject relative to said control population is indicative of ovarian neoplasia.

4. The method of claim 1, wherein said biological sample is selected from the group consisting of blood, plasma, serum, urine, follicular fluid, ascites, and saliva.

5. The method of claim 1, wherein said biological sample is serum.

6. The method of claim 1, wherein said biological sample is ascites.

7. The method of claim 1, wherein the level of proMBP is detected immunologically.

8. The method of claim 7, wherein the level of proMBP is detected using a capture antibody and a detection antibody, wherein said detection antibody comprises a label.

9. The method of claim 8, wherein said label is a fluorophore.

10. The method of claim 8, wherein said fluorophore is fluorescein, fluorescein isothiocyanate (FITC), phycoerythrin (PE), allophycocyanin (APC), or peridinin chlorophyll protein (PerCP).

11. The method of claim 8, wherein said label is biotin.

12. The method of claim 8, wherein said label is an enzyme.

13. The method of claim 8, wherein said label is a radioisotope.

14. The method of claim 8, wherein said capture antibody is attached to a solid substrate.

15. The method of claim 14, wherein said solid substrate is selected from the group consisting of a bead and a microtiter plate.

16. The method of claim 8, wherein said capture antibody is a polyclonal antibody.

17. The method of claim 8, wherein said detection antibody is a monoclonal antibody.

18. A method of monitoring treatment for ovarian cancer in a subject, said method comprising
    a) detecting the level of proMBP present in a biological sample from said subject, wherein said proMBP comprises the amino acid sequence set forth in SEQ ID NO:1; and
    b) comparing the level of proMBP in said sample to a baseline level of proMBP present in said subject before said treatment.

19. A method for monitoring a subject for recurrence of ovarian cancer, said method comprising
    a) detecting the level of proMBP present in a biological sample from said subject, wherein said proMBP comprises the amino acid sequence set forth in SEQ ID NO:1; and
    b) comparing the level of proMBP in said sample to a baseline level of proMBP present in said subject.

* * * * *